United States Patent [19]
Coffman et al.

[11] Patent Number: 5,676,940
[45] Date of Patent: Oct. 14, 1997

[54] METHOD OF REDUCING IMMUNOGLOBULIN E RESPONSES

[75] Inventors: Robert L. Coffman, Portola Valley, Calif.; Jan Egbert de Vries, Ecully, France

[73] Assignee: Schering Corporation, Kenilworth, N.J.

[21] Appl. No.: 210,649

[22] Filed: Mar. 17, 1994

Related U.S. Application Data

[63] Continuation of Ser. No. 033,996, Mar. 19, 1993, abandoned, which is a continuation of Ser. No. 774,366, Oct. 19, 1991, which is a continuation of Ser. No. 151,413, Feb. 2, 1988, abandoned.

[51] Int. Cl.$^6$ ............................................ A61K 45/05
[52] U.S. Cl. ........................................ 424/85.1; 424/85.2
[58] Field of Search ................................... 424/85.1, 85.2

[56] References Cited

U.S. PATENT DOCUMENTS

| | | | |
|---|---|---|---|
| 5,017,691 | 5/1991 | Lee et al. | 530/351 |
| 5,041,381 | 8/1991 | Abrams et al. | 435/240.27 |

FOREIGN PATENT DOCUMENTS 0230107  7/1987  European Pat. Off.

OTHER PUBLICATIONS

Bialy, *Bio/Technology*, Apr. 1986, pp. 614–621.
Casali, et al., *Science*, 234, 1986, pp. 476–479 (Ref. V: Paper No. 6, dated Jun. 26, 1990).
Coffman, et al., *Immune Regulation by Characterized Polypeptides* pp. 523–532 (Alan R. Liss, New York, 1987).
Coffman, et al., *J. Immunol.*, vol. 136, pp. 4538–4541 (1986).
Cruse, et al., *The Year in Immunology*, 1988, "Immunoregulatory Cytokines and cell Growth," ed, pp. 126–133.
Finkelman, t al., *Proc. Natl. Acad. Sci.*, vol. 83, pp. 9675–9678 (1986).
Guercio, et al., *Nature*, 329, 1987, pp. 445–447.
Hamaguchi, et al., *J. Exp. Med.*, 165, 1987, pp. 268–273.
Kikutani, et al. *Cell*, 47, 1986, pp. 657–665 (Ref. R: Paper No. 6, dated Jun. 26, 1990).
Langford, et al., "Antibody to Staphylococcal Enterotoxin A–induced Human Immune Interferon (IFNγ)" *The Journal of Immunology*, vol. 126, No. 4, Apr. 1981 pp. 1620–1623.
Mosmann, et al., *J. Immunol.*, vol. 138, pp. 1813–1816 (1987).
Pene, et al., *J. Immunol.*, vol. 141, pp. 1218–1224 (1988).
Snapper, et al., *Science*, vol. 236, pp. 944–947 (1987).
Snapper, et al., *Immunol. Rev.*, pp. 51–75 (1988).
Waldmann (1991) Science 252, 1657–1662.
Guercio, et al, *Nature* 329, 1987, pp. 445–447.
Casali et al *Science* 234, 1986, pp. 476–479.

*Primary Examiner*—Vasu S. Jagannathan
*Assistant Examiner*—Hyosuk Kim
*Attorney, Agent, or Firm*—Stephen C. Macevicz; Kenneth A. Weber; Edwin P. Ching

[57] ABSTRACT

A method of reducing immunoglobulin E responses associated with certain immune disorders is provided. The method comprises administering an effective amount of an antagonist to human interleukin-4. Preferably, the antagonist is a blocking monoclonal antibody specific for human interleukin-4, or a fragment or binding composition derived therefrom.

7 Claims, No Drawings

METHOD OF REDUCING IMMUNOGLOBULIN E RESPONSES

This application is a continuation of application Ser. No. 08/033,996 filed Mar. 19, 1993 now abandoned, on which application is a continuation of application of Ser. No. 07/774,366 filed Oct. 9, 1991.

FIELD OF THE INVENTION

The invention relates generally to a method for treating immune diseases associated with excessive production of immunoglobulin E (IgE), and more particularly, to a method of inhibiting IgE production by inhibiting the action of interleukin-4.

BACKGROUND

As far as can be determined, the main physiological function of IgE-mediated responses is to combat parasites. The response can be divided into five phases: an IgE-bearing B cell is stimulated to respond to an antigen (phase 1) and activated to secrete IgE antibodies (phase 2), the produced antibodies bind to mast cells and basophils in tissues (phase 3, antibody fixation), interaction of allergen with cell-bound IgE activates these cells, and causes the release of chemical mediators stored in their granules (phase 4, degranulation); and finally, the mediators induce a complex tissue response aimed at the elimination of nonmicrobial parasites from the body (phase 8). Part of this defense mechanism is an attack on the tissue that harbors the parasite—that is, on self. To excise a parasite from a tissue without damaging the rest of the body is an extraordinarily delicate act. The mediators released by activated mast cells and basophils can cause considerable harm, even death, if released at an inappropriate time or if directed at an inappropriate target. The IgE response must be closely controlled and quickly attenuated after its goal has been achieved. As long as this control is functioning there is no danger that healthy parts of the body will be damaged, but should the controls fail, the beneficial reaction will turn into a harmful one. In humans, about 90 percent of all individuals have no difficulty in using their IgE only for defensive purposes; but the remaining unlucky 10 percent carry a genetic defect of the control mechanism that permits the stimulation of IgE responses by antigens that have nothing to do with parasites. At first it was thought that this defect was limited only to humans, but similar defects were discovered later in several other mammals. The inappropriately stimulated IgE responses cause a plethora of diverse diseases, grouped under the name allergy or atopy, Klein, *Immunology: The Science of Self-Nonself Discrimination* (John Wiley & Sons, New York, 1982).

Currently glucocorticoid steroids are the most effective drugs for treating allergic diseases. However prolonged steroid treatment is associated with many deleterious side effects, Goodman and Gillman, *The Pharmacological Basis of Therapeutics*, 6th ed. (MacMillan Publishing Company, New York, 1980). Consequently, the availability of alternative approaches to the treatment of immune disorders associated with excessive IgE production could have important clinical utility.

SUMMARY OF THE INVENTION

The invention is a method of reducing levels of IgE by administering an effective amount of an antagonist to human interleukin-4 (IL-4). Preferably, the antagonists to IL-4 are monoclonal antibodies, or binding compositions derived therefrom by standard techniques.

DETAILED DESCRIPTION OF THE INVENTION

The invention is based on the discovery that IL-4 increases the production of IgE in humans. The method of the invention comprises administering to an individual an effective, or disease-ameliorating amount, of an antagonist to human IL-4.

Preferably, the antagonists of the invention are derived from antibodies specific for human IL-4. More preferably, the antagonists of the invention comprise fragments or binding compositions specific for IL-4.

Antibodies comprise an assembly of polypeptide chains linked together by disulfide bridges. Two major polypeptide chains, referred to as the light chain and the heavy chain, make up all major structural classes (isotypes) of antibody. Both heavy chains and light chains are further divided into subregions referred to as variable regions and constant regions. Heavy chains comprise a single variable region and three different constant regions, and light chains comprise a single variable region (different from that of the heavy chain) and a single constant region (different from those of the heavy chain). The variable regions of the heavy chain and light chain are responsible for the antibody's binding specificity.

As used herein, the term "heavy chain variable region" means a polypeptide (1) which is from 110 to 125 amino acids in length, and (2) whose amino acid sequence corresponds to that of a heavy chain of a monoclonal antibody of the invention, starting from the heavy chain's N-terminal amino acid. Likewise, the term "light chain variable region" means a polypeptide (1) which is from 95 to 115 amino acids in length, and (2) whose amino acid sequence corresponds to that of a light chain of a monoclonal antibody of the invention, starting from the light chain's N-terminal amino acid.

As used herein the term "monoclonal antibody" refers to homogenous populations of immunoglobulins which are capable of specifically binding to human IL-4.

As used herein the term "binding composition" means a composition comprising two polypeptide chains (1) which, when operationally associated, assume a conformation having high binding affinity for human interleukin-4, and (2) which are derived from a hybridoma producing monoclonal antibodies specific for human interleukin-4. The term "operationally associated" is meant to indicate that the two polypeptide chains can be positioned relative to one another for binding by a variety of means, including by association in a native antibody fragment, such as Fab or Fv, or by way of genetically engineered cystiene-containing peptide linkers at the carboxyl termini. Normally, the two polypeptide chains correspond to the light chain variable region and heavy chain variable region of a monoclonal antibody specific for human interleukin-4.

Preferably, antagonists of the invention are derived from monoclonal antibodies specific for human IL-4. Monoclonal antibodies capable of blocking IgE-enhancing activity of IL-4 are selected in standard in vitro assays for IL-4 based on T cell proliferation, e.g. Yokota et al. (cited above). It has been observed in murine systems that all biological activities of IL-4 can be blocked by a single monoclonal antibody. Thus, it is believed that all the activities are mediated by a single site, e.g. the receptor binding site, on the protein.

Hybridomas of the invention are produced by well known techniques. Usually, the process involves the fusion of an immortalizing cell line with a B-lymphocyte which produces the desired antibody. Alternatively, non-fusion techniques for generating an immortal antibody producing cell lines are possible, and come within the purview of the present invention, e.g. virally induced transformation: Casali et al., "Human Monoclonals from Antigen-Specific Selection of B Lymphocytes and Transformation by EBV," *Science*, Vol. 234, pgs. 478–479 (1988). Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining the appropriate lymphocytes from mammals injected with the target antigen are well known. Generally, either peripheral blood lymphocytes (PBLs) are used if cells of human origin are desired, or spleen cells or lymph node cells are used if non-human mammalian sources are desired. A host mammal is injected with repeated dosages of the purified antigen, and the mammal is permitted to generate the desired antibody producing cells before these are harvested for fusion with the immortalizing cell line. Techniques for fusion are also well known in the art, and in general, involve mixing the cells with a fusing agent, such as polyethylene glycol. Hybridomas are selected by standard procedures, such as HAT selection. From among these hybridomas, those secreting the desired antibody are selected by assaying their culture medium by standard immunoassays, such as Western blotting, ELISA, RIA, or the like. Antibodies are recovered from the medium using standard protein purification techniques, e.g. Tijssen, *Practice and Theory of Enzyme Immunoassays* (Elsevier, Amsterdam, 1985). Many references are available for guidance in applying any of the above techniques, e.g. Kohler et al., *Hybridoma Techniques* (Cold Spring Harbor Laboratory, New York, 1980); Tijssen, *Practice and Theory of Enzyme Immunoassays* (Elsevier, Amsterdam, 1988); Campbell, *Monoclonal Antibody Technology* (Elsevier, Amsterdam, 1984); Hurrell, *Monoclonal Hybridoma Antibodies: Techniques and Applications* (CRC Press, Boca Raton, Fla. 1982); and the like.

The use and generation of fragments of antibodies is also well known, e.g. Fab fragments: Tijssen, *Practice and Theory of Enzyme Immunoassays* (Elsevier, Amsterdam, 1985); and Fv fragments: Hochman et al. *Biochemistry*, Vol. 12, pgs. 1130–1135 (1973), Sharon et al., *Biochemistry*, Vol. 15, pgs. 1591–1594 (1976) and Ehrlich et al., U.S. Pat. No. 4,355,023; and antibody half molecules: Auditore-Hargreaves, U.S. Pat. No. 4,470,925. Moreover, such compounds and compositions of the invention can be used to construct hi-specific antibodies by known techniques, e.g., via further fusions of hybridomas (i.e. to form so-called quadromas), Reading, U.S. Pat. No. 4,474,493; or via chemical reassociation of half molecules, Brennan et al., *Science*, Vol. 229, pgs. 81–83 (1985).

Hybridomas and monoclonal antibodies of the invention are produced against either glycosylated or unglycosylated versions of recombinantly produced mature human interleukin-4. Generally, unglycosylated versions of human IL-4 are produced in *E. coli*, and glycosylated versions are produced in mammalian cell hosts, e.g. CV1 or COS monkey cells, mouse L cells, or the like. Recombinantly produced mature human IL-4 is produced by introducing an expression vector into a host cell using standard protocols, e.g. Maniatis et al., *Molecular Cloning: A Laboratory Manual* (Cold Spring Harbor Laboratory, New York, 1982); Okayama and Berg, *Mol. Cell. Biol.*, Vol. 2, pgs. 161–170 (1982) and Vol. 3, pgs. 280–289 (1983); Hamer, *Genetic Engineering*, Vol. 2, pgs. 83–100 (1980) and U.S. Pat. No. 4,599,308; Kaufman et al., *Mol. Cell. Biol.*, Vol. 2, pgs. 1304–1319 (1982); or the like.

Construction of bacterial or mammalian expression vectors are well known in the art, once the nucleotide sequence encoding a desired protein is known or otherwise available, e.g. DeBoer in U.S. Pat. No. 4,551,433 discloses promoters for use in bacterial expression vectors; Goeddel et al., in U.S. Pat. No. 4,601,980, and Riggs, in U.S. Pat. No. 4,431,739 disclose the production of mammalian proteins by *E. coli* expression systems; and Riggs (cited above), Ferretti et al., *Proc. Natl. Acad. Sci.*, Vol. 83, pgs. 599–603 (1986), Sproat et al., *Nucleic Acids Research*, Vol. 13, pgs. 2959–2977 (1985), and Mullenbach et al., *J. Biol. Chem.*, Vol. 261, pgs. 719–722 (1986) disclose how to construct synthetic genes for expression in bacteria. Accordingly, these references are incorporated by reference. The amino acid sequence of mature human IL-4 is disclosed by Yokota et al. (cited above), and the cDNA encoding human IL-4 carried by the pcD vector described in Yokota et al. (cited above) is deposited with the American Type Culture Collection (ATCC), Rockville, Md., under accession number 67029. Many bacterial expression vectors and hosts are available commercially and through the ATCC. Preferably, human IL-4 for immunizing host animals is isolated from culture supernatants of COS, CV1, or mouse L cells which have been transiently transfected by the above-mentioned pcD vector.

Antibodies and antibody fragments characteristic of hybridomas of the invention can also be produced by recombinant means by extracting messenger RNA, constructing a cDNA library, and selecting clones which encode segments of the antibody molecule, e.g. Wall et al., *Nucleic Acids Research*, Vol. 5, pgs. 3113–3128 (1978); Zakut et al., *Nucleic Acids Research*, Vol. 8, pgs. 3591–3601 (1980); Cabilly et al., *Proc. Natl. Acad. Sci.*, Vol. 81, pgs. 3273–3277 (1984); Boss et al., *Nucleic Acids Research*, Vol. 12, pgs. 3791–3806 (1984); Amster et al., *Nucleic Acids Research*, Vol. 8, pgs. 2055–2065 (1980); and Moore et al., U.S. Pat. No. 4,642,334. In particular, such techniques can be used to produce interspecific monoclonal antibodies, wherein the binding region of one species is combined with non-binding region of the antibody of another species to reduce immunogenicity, e.g. Liu et al., *Proc. Natl. Acad. Sci.*, Vol. 84, pgs. 3439–3443 (1987).

Antagonists of the invention are administered as a pharmaceutical composition. Such compositions contain a therapeutic mount of at least one of the monoclonal antibodies of the invention, or fragments thereof, in a pharmaceutically effective carrier. A pharmaceutical carrier can be any compatible, non-toxic substance suitable for delivering the compositions of the invention to a patient. Sterile water, alcohol, fats, waxes, and inert solids may be included in a carrier. Pharmaceutically accepted adjuvants (buffering agents, dispersing agents) may also be incorporated into the pharmaceutical composition. Generally, compositions useful for parenteral administration of such drugs are well known, *Remington's Pharmaceutical Science*, 15th Ed. (Mack Publishing Company, Easton, Pa. 1980). Alternatively, compositions of the invention may be introduced into a patient's body by implantable drug delivery system, e.g. Urquhart et al., *Ann. Rev. Pharmacol. Toxicol.*, Vol. 24 pgs. 199–236 (1984).

When the antagonists of the inventions are derived from antibodies, they are normally administered parentally, preferably intravenously. Since such protein or peptide antagonists may be immunogenic they are preferably administered slowly, either by a conventional IV administration set or from a subcutaneous depot.

When administered parenterally the antibodies or fragments will be formulated in a unit dosage injectable form (solution, suspension, emulsion) in association with pharmaceutically acceptable parenteral vehicle. Such vehicles are inherently nontoxic and nontherapeutic. Examples of such vehicles are normal saline, Ringer's solution, dextrose solution, and Hank's solution. Nonaqueous vehicles such as fixed oils and ethyl oleate may also be used. A preferred vehicle is 6% dextrose/saline. The vehicle may contain minor amounts of additives such substances that enhance isotonicity and chemical stability, e.g., buffers and preservatives. The antibody is preferably formulated in purified form substantially free of aggregates and other proteins at concentrations of about 5 to 30 mg/ml, preferably 10 to 20 mg/ml.

Selecting an administration regimen for an antagonist depends on several factors, including the serum turnover rate of the antagonist, the serum level of IL-4 associated with the immune disorder, the immunogenicity of the antagonist, the accessibility of the target IL-4 (e.g. if non-serum IL-4 is to be blocked), the relative affinity of IL-4 to its receptor(s) versus IL-4 to the antagonist, and the like. Preferably, an administration regimen maximizes the amount of antagonist delivered to the patient consistent with an acceptable level of side effects. Accordingly, the amount of antagonist delivered depends in part on the particular antagonist and the severity of the disease being treated. Guidance in selecting appropriate doses is found in the literature on therapeutic uses of antibodies, e.g. Bach et al., chapter 22, in Ferrone et al., eds., *Handbook of Monoclonal Antibodies* (Noges Publications, Park Ridge, N.J., 1985); and Russell, pgs. 303–357, and Smith et al., pgs. 365–389, in Haber et al., eds. *Antibodies in Human Diagnosis and Therapy* (Raven Press, New York, 1977). Preferably, whenever the antagonist comprises monoclonal antibodies or Fab-sized fragments thereof (including binding compositions), the dose is in the range of about 1–20 mg/kg per day. More preferably the dose is in the range of about 1–10 mg/kg per day.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

Applicants have deposited *E. coli* MC1061 carrying pcD-human-IL4 with the American Type Culture Collection, Rockville, Md., USA (ATCC), under accession number 67029. This deposit was made under conditions as provided under ATCC's agreement for Culture Deposit for Patent Purposes, which assures that the deposit will be made available to the US Commissioner of Patents and Trademarks pursuant to 35 USC 122 and ST CFR 1.14, and will be made available to the public upon issue of a U.S. patent, which requires that the deposit be maintained. Availability of the deposited strain is not to Be construed as a license to practice the invention in contravention of the rights granted under the authority of any government in accordance with its patent laws.

We claim:

1. A method of reducing an immunoglobulin E response in an individual comprising administering to said individual exhibiting an immunoglobulin E response an effective amount of an antagonist to human interleukin-4, selected from the group consisting of:

a) an intact antibody;

b) an antibody half molecule;

c) an Fab fragment; and d) an Fv fragment;

said amount effective to reduce said response.

2. The method of claim 1, wherein said antagonist comprises an immunoglobulin heavy chain variable region.

3. The method of claim 2, wherein said antagonist further comprises an immunoglobulin light chain variable region.

4. The method of claim 1, wherein said antibody is a monoclonal antibody.

5. The method of claim 1, wherein said administering is intravenous.

6. The method of claim 1, wherein said antagonist is administered in the range of about 1–20 mg/kg body weight of said individual per day.

7. The method of claim 1, wherein said response is an allergic or atopic response.

* * * * *